(12) United States Patent
Carrat et al.

(10) Patent No.: US 9,572,539 B2
(45) Date of Patent: Feb. 21, 2017

(54) DEVICE AND METHOD FOR DETERMINING THE POSITION OF AN INSTRUMENT IN RELATION TO MEDICAL IMAGES

(75) Inventors: Lionel Carrat, Saint Martin d'Here (FR); Stéphanie Lavallee, St. Martin d'Uriage (FR)

(73) Assignee: IMACTIS, La Tronche (FR)

( * ) Notice: Subject to any disclaimer, the term of this patent is extended or adjusted under 35 U.S.C. 154(b) by 1065 days.

(21) Appl. No.: 13/441,736

(22) Filed: Apr. 6, 2012

(65) Prior Publication Data

US 2012/0259204 A1    Oct. 11, 2012

Related U.S. Application Data

(60) Provisional application No. 61/473,235, filed on Apr. 8, 2011.

(51) Int. Cl.
*A61B 6/00* (2006.01)
*A61B 6/12* (2006.01)
(Continued)

(52) U.S. Cl.
CPC ............ *A61B 6/12* (2013.01); *A61B 5/061* (2013.01); *A61B 6/584* (2013.01); *A61B 34/20* (2016.02); *A61B 6/032* (2013.01); *A61B 6/487* (2013.01); *A61B 42/00* (2016.02); *A61B 90/30* (2016.02); *A61B 90/361* (2016.02); *A61B 2017/00438* (2013.01); *A61B 2017/00725* (2013.01);
(Continued)

(58) Field of Classification Search
CPC ............... A61B 19/5244; A61B 2019/5287; A61B 2019/5255; A61B 2019/5272; A61B 2019/5483; A61B 2019/5212; A61B 6/12; A61B 6/584; A61B 6/032; A61B 6/487; A61B 5/061; A61B 34/20; A61B 2017/00438; A61B 2017/00725; A61B 90/30; A61B 90/361; A61B 2090/364; A61B 2090/371; A61B 2090/3937; A61B 42/00
See application file for complete search history.

(56) References Cited

U.S. PATENT DOCUMENTS 5,851,183 A * 12/1998 Bucholz ............... A61B 5/0064
600/424
6,529,765 B1 * 3/2003 Franck et al. ............... 600/427
(Continued)

OTHER PUBLICATIONS

Borgefors; "Hierarchical Chamfer Matching: A Parametric Edge Matching Algorithm"; Nov. 1988; IEEE Transactions on Pattern Analysis and Machine Intelligence; vol. 10; No. 6; pp. 849-865.
(Continued)

*Primary Examiner* — Elmer Chao
(74) *Attorney, Agent, or Firm* — Blakely Sokoloff Taylor & Zafman LLP

(57) ABSTRACT

The present invention relates to a device and a method for determining the position of an instrument with respect to medical images of a body. The device comprises (1) a calibration support comprising a set of fiducial markers visible on medical images and fixed to the skin of a body, (2) at least one micro-camera providing video images and mounted on the calibration support in a known position, and (3) a processing unit connected to the micro-cameras and configured to process the video images from said micro-cameras to determine the position of the instrument with respect to medical images.

11 Claims, 13 Drawing Sheets

(51) Int. Cl.
*A61B 5/06* (2006.01)
*A61B 6/03* (2006.01)
*A61B 17/00* (2006.01)

(52) U.S. Cl.
CPC ... *A61B 2090/364* (2016.02); *A61B 2090/371* (2016.02); *A61B 2090/3937* (2016.02)

(56) References Cited

U.S. PATENT DOCUMENTS

| | | |
|---|---|---|
| 6,675,040 B1 * | 1/2004 | Cosman ................. 600/427 |
| 7,876,942 B2 | 1/2011 | Gilboa |
| 2008/0097155 A1 * | 4/2008 | Gattani et al. ............ 600/117 |

OTHER PUBLICATIONS

Huttenlocher et al.; "Recognizing Solid Objects by Alignment with an Image"; 1990; vol. 5; No. 2; pp. 195-212.

Lavallee et al.; "Recovering the Position and Orientation of Free-Form Objects from Image Contours Using 3D Distance Maps"; Apr. 1995; IEEE Transactions on Pattern Analysis and Machine Intelligence; vol. 17; No. 4.

Maintz et al.; "A survey of medical image registration"; 1998; Medical Image Analysis; vol. 2; No. 1; pp. 1-36.

Szeliski; "Computer Visions: Algorithms and Applications"; 2011; Springer, Texts in Computer Science; (see chapter "Feature Detection and matching", pp. 181-227).

\* cited by examiner

DEVICE AND METHOD FOR DETERMINING THE POSITION OF AN INSTRUMENT IN RELATION TO MEDICAL IMAGES

CROSS REFERENCE TO RELATED APPLICATION

This application claims priority to U.S. Provisional Application No. 61/473,235, filed Apr. 8, 2011, the content of which is incorporated herein by reference in its entirety.

BACKGROUND

Field of the Invention

The present invention relates to a device and a method for determining the position of an instrument in relation to medical images.

Description of Related Art

Navigation systems are commonly tracking instrument position and orientation with respect to medical images of a body. Conventional tracking devices are made of optical devices, magnetic devices, ultrasonic devices, inclinometers, and accelerometers, radio-frequency measurement devices, used independently or in combination. In optical systems, tracking the position of an instrument is usually achieved by placing emitters or reflectors on both the instrument and on the body reference and observing the scene with two or three cameras. The most widely used system is the Polaris device manufactured by the company Northern Digital Inc; (Waterloo, Ontario, Canada). Existing optical localization devices are expensive and cumbersome, or not accurate enough.

Magnetic localization devices such as Aurora from the company Northern Digital Inc. (Waterloo, Ontario Canada) are compact but they are expensive; in addition, they require special care in environments with the presence of metallic objects such as the examination table or magnetic objects that constitute the core of magnetic resonance imaging devices, which may lead to inaccurate measurements.

Coming back to optical systems, video images can be used to detect the position and orientations of different types of objects, using one camera, or two cameras in stereoscopic systems, or even multiple cameras to add accuracy and robustness to measurements. In particular, in U.S. Pat. No. 7,876,942 from Gilboa, one or several micro-cameras are rigidly fixed to a needle wherein the micro-cameras observe at the same time the needle and a calibration target that is used as a reference phantom mounted on a body, said reference phantom being visible on medical images of the body. But this device requires equipping a needle with cameras which adds weight to the needle and that operators do not appreciate. In addition, if a micro-camera is mounted on a needle, the positions of the fingers and hands must be such to avoid the occlusions of the reference phantom, which adds complexity instead of providing a simple assistance to the operator. This is not a fluid process.

There is therefore a need for a method and device that can track the position of an instrument with respect to medical images of a body that is very easy to use with low constraints and that can be used in environments with metallic or magnetic objects.

Algorithms to detect and locate in three dimensions an object made of points and lines, or objects with a known geometry, or hands and fingers, from one or several video images have been developed for many years in the literature of computer vision and many variations exist. This is often referred to as stereoscopic measurements and detection although three or more cameras can be used instead of two. The theory of computer vision with only one camera is also well known and falls in the category of stereoscopy. One can refer for example to the basic principles exposed in "D. P. Huttenlocher and S. Ullman. *Recognizing Solid Objects by Alignment with an Image. International Journal of Computer Vision,* 5(2):195-212, 1990" or in "G. Borgefors. *Hierarchical Chamfer Matching: A Parametric Edge Matching Algorithm. IEEE Transactions on Pattern Analysis and Machine Intelligence,* 10(6):849-865, 1988" or in "S. Lavallée and R. Szeliski. *Recovering the position and orientation of free-form objects from image contours using* 3-D *distance maps. IEEE PAMI (Pattern Analysis and Machine Intelligence),* 17(4):378-390, 1995" or in the textbook "R. Szeliski. *Computer Vision: Algorithms and Applications, Springer, Texts in Computer Science,* 2011". Several standard packages are also available for using common computer vision algorithms such as for instance "The Machine Vision Toolbox" which is available on the web site http://www.ict.csiro.au/downloads.

For example, a package for automatic calibration of video cameras using calibration grids is available on: http://www.vision.caltech.edu/bouqueti/calib doc/htmls/example.html or also in http://www.vision.ee.ethz.ch/software/calibration toolbox//calibration toolbox.php. However, those algorithms provide basic tools and components that any system in computer vision uses commonly, but they fail to provide a solution to the specific problem mentioned above.

SUMMARY

The invention is proposed to solve the drawbacks exposed in the Background section. It proposes a method and device that can track the position of an instrument with respect to medical images of a body that is very easy to use with low constraints and that can be used in environments with metallic or magnetic objects. The method of the invention is used for determining the position of an instrument with respect to medical images of a body, the method comprising the steps of:

(a) placing a calibration support comprising fiducial markers on the skin of the body in the intended region of interest;

(b) acquiring the medical images of the body with calibration support in place;

(c) detecting the fiducial markers on the medical images to determine the geometric relationship between a coordinate system attached to the medical images and a coordinate system attached to the calibration support;

(d) connecting rigidly at least one micro-camera to the calibration support at a known position;

(e) placing an instrument in the field of view of the cameras;

(f) detecting the instrument in the video images of the cameras (g) calculating the position of the instrument in a coordinate system attached to the cameras using the calibration of each camera in the coordinate system of the calibration support; and (h) transferring the position of the instrument in the coordinate system attached to the medical images using the result of step (c).

The method further comprises a step of displaying the position of the instrument on medical images. In a preferred embodiment, the instrument has a linear shape and two reformatted images passing through the linear instrument axis are computed in the volume of medical images and displayed.

In a particular embodiment, the calibration of the camera is determined by a method that comprises the steps of:
(a) connecting to the calibration support a calibration phantom that comprises an extension bar and a plurality of markers rigidly connected to the extension bar and visible on the video images obtained from the micro-cameras and spatially arranged in a known position that can be recognized in a unique manner in a phantom coordinate system;
(b) acquiring video images of the markers of the calibration phantom;
(c) determining the projection matrix for each micro-camera using the known coordinates of the markers in the phantom coordinate system;
(d) transferring the projection matrix of each camera in the calibration support coordinate system by using the geometric matrix between the calibration support coordinate system and the phantom coordinate system determined by metrological measurements performed when the calibration support and the calibration phantom are connected together.

For obtaining reliable and precise positions, the method further comprises the step of reinforcing the visibility of the instrument for its detection using one or several of the following means:
(a) adding an infrared light system to the cameras
(b) adding a background element with a known color behind the instrument For obtaining reliable detection of the instrument on video images, the method of the invention further comprises the step of reinforcing the detection of the instrument using a reinforced visibility element in relation to the instrument, said reinforced visibility element having one or several of the following features:
(a) a specific and known color
(b) a specific and known shape
(c) a specific and known pattern
(d) a specific and known dimension.

The method also comprises an instrument that has a known internal axis that guides a needle and an external reinforced visibility element made of an external shape that is colored, complex, and specific.

In most situations, the instrument is a conventional needle and the needle axis is detected on video images by searching for long and thin objects in the video images.

To gain precision when the instrument is flexible, the deformation of the instrument axis is determined and reconstructed in three dimensions for use in either one or several of the following modes:
(a) inform the user about excessive instrument deformation
(b) extend instrument deformation measured externally inside the body to predict and display the trajectory of the instrument on medical images.

Another object of the invention is a device for determining the position of an instrument with respect to medical images of a body, the device comprising:
(a) a calibration support comprising a set of fiducial markers visible on medical images and adapted to be fixed to the skin of a body;
(b) at least one micro-camera providing video images and mounted on the calibration support in a known position;
(c) a processing unit connected to the micro-cameras and configured to process video images from said micro-cameras to determine the position of the instrument with respect to medical images.

According to a first embodiment of the invention, two micro-cameras forming an angle of less than ninety degrees between them are fixed to the calibration support.

According to a second embodiment, three micro-cameras forming an angle of less than ninety degrees between them are fixed to the calibration support.

The device further advantageously comprises a background support adapted to be attached to the skin of the body and contrasting with the instrument to reinforce the visibility of the instrument on the video images.

The background support and the calibration support may be rigidly connected and the background support may comprise markers at known positions that are used to calibrate the micro-cameras.

According to a particular embodiment of the invention, the calibration support is a circular and rigid ring on which at least four micro-cameras are mounted.

In this case, the circular and rigid ring advantageously comprises a background cylinder contrasting with the instrument so as to reinforce the visibility of the instrument on the video images.

Besides, the device according to the invention may comprise a reinforced visibility element that is more visible on the video images than the instrument and the instrument has an axis that has known geometric relationship with respect to said reinforced visibility element.

Said reinforced visibility element may be directly engraved on the instrument surface.

Alternatively, said reinforced visibility element is a reinforced visibility ring having a donut shape and the instrument has a linear part passing through the hole of the reinforced visibility ring.

Alternatively, said reinforced visibility element comprises a reinforced visibility cylindrical guide and the instrument has a linear part passing through the reinforced visibility cylindrical guide, which may be equipped with a handle.

In particular, said reinforced visibility element may be a reinforced visibility guiding device that has a known geometry between its external visible surface and guiding elements of the linear part of the instrument.

Said guiding device may have a clothes peg shape wherein the articulated branches of the peg comprise a V-shaped groove for guiding the linear part of the instrument.

According to another embodiment of the invention, said reinforced visibility element comprises at least one reinforced visibility glove finger extremity.

The calibration support may comprise a lower adhesive surface adapted to adhere temporarily to the skin of the body and/or a suction pad so as to adhere temporarily to the skin of the body.

In a preferred embodiment of the invention, the device comprises a semi-rigid element placed between the calibration support and a lower surface adapted to adhere temporarily to the skin of the body, such that said semi-rigid element conforms to the shape of the skin.

The micro-cameras may be embedded into the calibration support.

Alternatively, the micro-cameras are removably attached to the calibration support by an intermediate basis.

The micro-cameras may be equipped with a lighting system adapted to light the instrument so as to reinforce the visibility of the instrument on the video images.

Said lighting system is preferably emitting light in a non visible infra-red spectrum.

According to an embodiment of the invention, the fiducial markers comprise at least three spherical balls spatially arranged in a known position that can be recognized in a unique manner.

The fiducial markers may also comprise at least two non-parallel cylindrical tubes spatially arranged in a known position that can be recognized in a unique manner.

The fiducial markers may comprise a combination of cylindrical tubes, cylindrical discs and spherical balls arranged in a known position that can be recognized in a unique manner.

The medical images may be computed tomography images, and/or magnetic resonance images (the cameras being protected by an appropriate shielding) and/or 2D x-ray images.

According to an embodiment of the invention, the device further comprises a calibration phantom for determining the geometric relationship between the calibration support and the micro-cameras, wherein said calibration phantom comprises:
(a) an extension bar connected in a reproducible and known manner to the calibration support;
(b) a plurality of video calibration markers rigidly connected to the extension bar and visible on the video images obtained from the micro-cameras and spatially arranged in a known position that can be recognized in a unique manner.

DETAILED DESCRIPTION OF A PREFERRED EMBODIMENT

Figure 1:
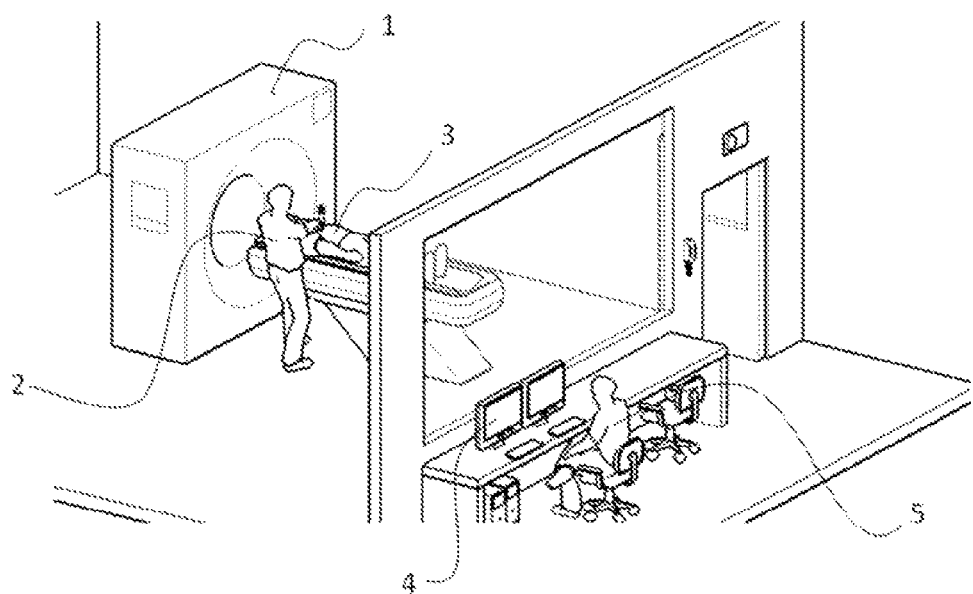
FIG. 1 is a schematic view that represents the body during a 3D image examination and the related equipments.

The present invention provides a device and method for tracking the position of a hand-held conventional instrument with respect to medical images of a body. The instrument is generally a needle or a linear guide to insert a needle like a surgical trocar. The rest of the text uses the term "instrument" to refer to a sharp and thin long instrument that is inserted into a body for delivering or extracting materials or energy, like biopsy trocars, needles, e.g. injection needles, radio-frequency probes, cryogenics probes, drains, K-wires, and rigid or semi-rigid trocars. The principles and operations of the device and method according to the present invention may be better understood with reference to the drawings and the accompanying description.

The present invention provides a device and a method for measuring the position and orientation of an instrument, which can be straight or bended, with respect to medical images of a body. A calibration support comprising a set of fiducial markers visible on medical images is fixed to the skin of a body. Medical images of the body are generated in three dimensions, they are typically Computed Tomography images, also known as CT scans, or Magnetic resonance images (MR), or 3D Fluoroscopy images obtained with a device such as the ISOC-3D ORBIC manufactured by Siemens (Erlangen, Germany). One or several micro-cameras are fixed to the calibration support and they are connected via conventional means, using wires or wireless connection, to a conventional computer such as PC or laptop computer. Micro-cameras can be conventional WEB CAMS or the miniature cameras that are commonly contained in smart phones with a specific packaging suitable for medical use. They can use CCD or CMOS technologies. In a preferred embodiment, micro-cameras provide color images. They provide digital images in a format such as 640×480 pixels for instance that is stored in the RAM memory of the computer at a frame rate of several images per second (typically 10 or 25 images per second). Dedicated software installed on the computer can detect the trace of an instrument that is hand held and placed in the field of view of the micro-cameras. Such software determines the position, orientation and optionally bending of said instrument in the coordinate system of the micro-cameras. The same computer collects the 3D images of the body via a standard DICOM network and a second software program runs to detect automatically the fiducial markers contained in the calibration support. This processing provides a geometric transform between the body image coordinate system and the calibration support coordinate system. The micro-cameras are calibrated geometrically with respect to the calibration support, therefore the geometric transform between the micro-cameras coordinate system and the calibration support coordinate system is known. Finally, the position, orientation and optional bending of the instrument is determined in the coordinate system of the body images. Then, a display monitor connected to the computer is used to show the position of the instrument in relation with the organs visible on the images of the body. Before inserting the instrument in the body, the user can see the trajectory of the instrument on the body images and adjust its position and orientation accordingly.

At this stage, it will already be apparent that the system and method offer major advantages over the aforementioned prior art. Specifically, by using micro-cameras directly mounted on the skin of a body and connected rigidly to a calibration support, said micro-cameras being connected to a conventional computer, it is possible to measure and determine the position of any conventional instrument in relation to the images of a body, using very cheap components that can be found off-the-shelf and with a manipulation that is very easy and transparent for the user. The handling of the instrument remains mostly unchanged compared to traditional use and no weight is added to the instrument. This and other advantages of the present invention will become clearer from the subsequent detailed description.

The general setup of the invention is shown in FIG. 1. An imaging device 1 is used to generate 3D images of a body, which can be CT, MR, 3D Fluoroscopy or more generally and type of images that produce voxel elements like SPECT, PET, or MEG imaging. Note also that the imaging device 1 can be also a simple 2D imaging device and that the method described below will still be applicable but with the restriction that the instrument will have to be projected on 2D images produced by the device instead of a precise 3D representation of the instrument trajectory on slices reformatted in the volume of 3D images. For simplicity, we limit the description to 3D images. The operator 2 is standing on the side of the body 3 which is lying on an examination table which can be translated back and forward in and out the imaging device 1. The medical images of the body are calculated in or transferred to the medical imaging computer 4. An assistant 5 controls the use of the imaging device. Note that FIG. 1 shows only the context of use of the invention. The device of the invention is not represented on FIG. 1.

Figure 2:
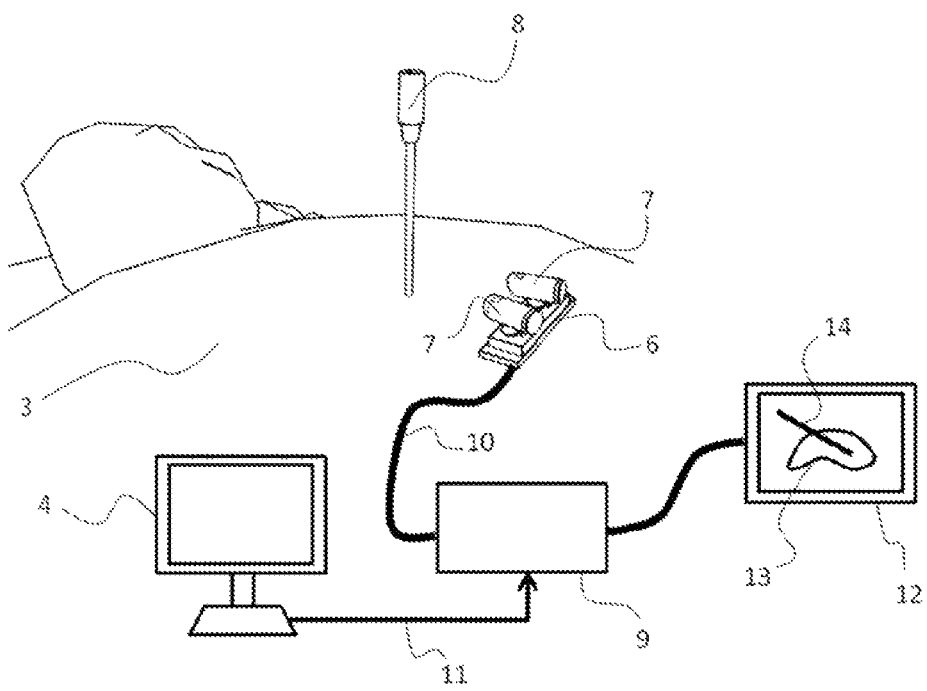
FIG. 2 is a schematic view of the device of the invention.
Figure 7:
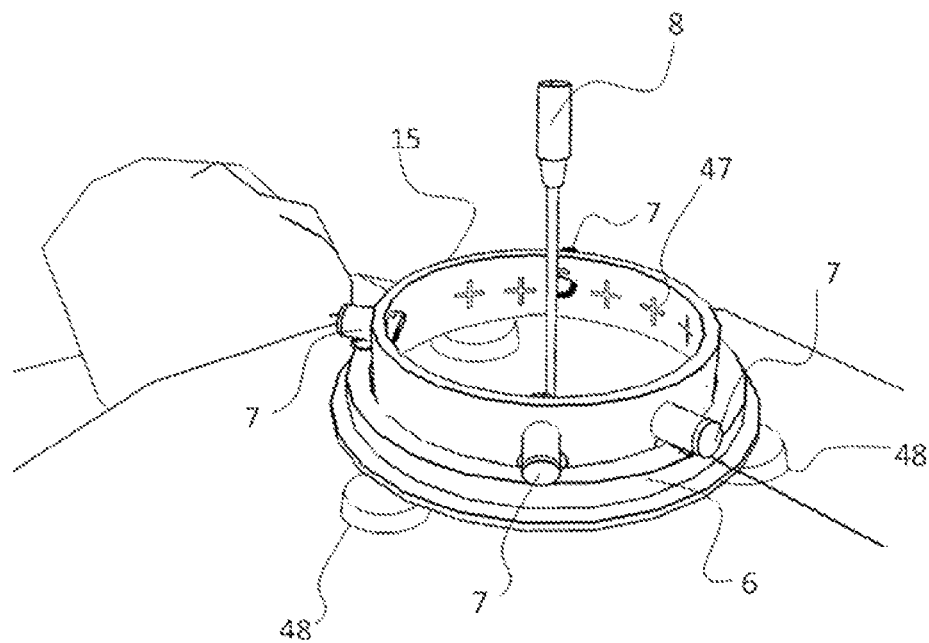
FIG. 7 is a schematic view of another preferred embodiment of the invention with four micro-cameras and a background support.
Figure 14:
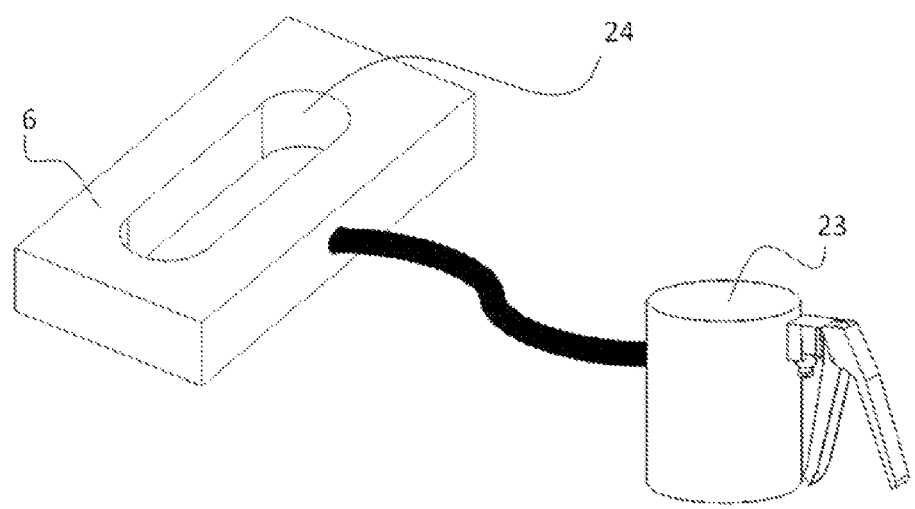
FIG. 14 is a schematic view of a preferred embodiment of the invention wherein a calibration support is fixed to the skin with a suction device.
Figure 15:
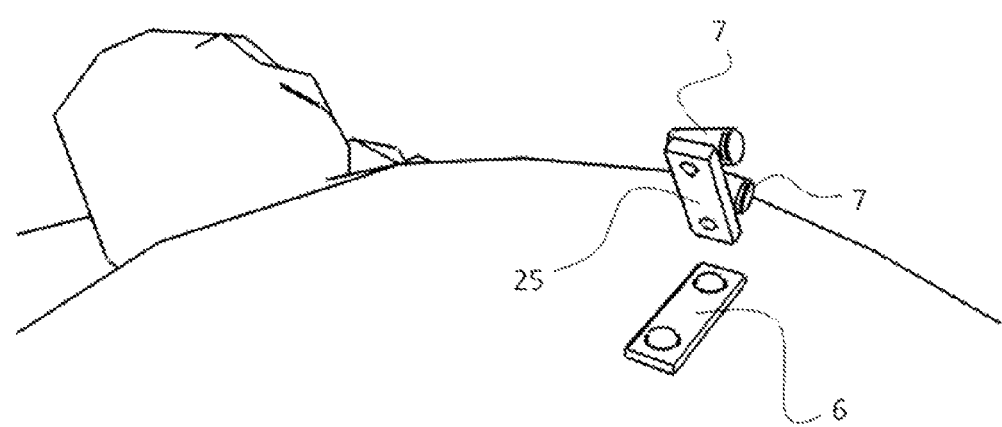
FIG. 15 is a schematic view of a preferred embodiment of the invention wherein the calibration support is detachable from the micro-cameras.
Figure 16:
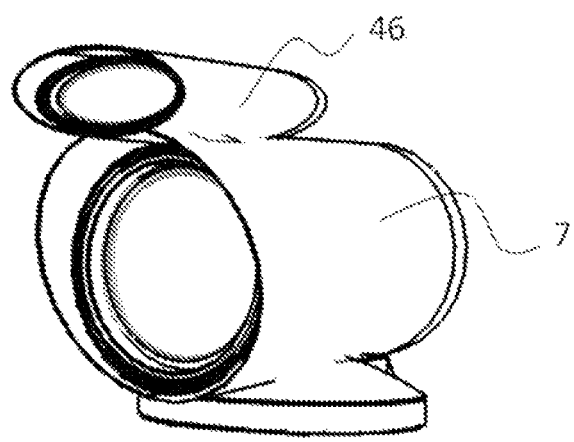
FIG. 16 is a schematic view of a preferred embodiment of the invention wherein the micro-camera is equipped with a light.
Figure 21:
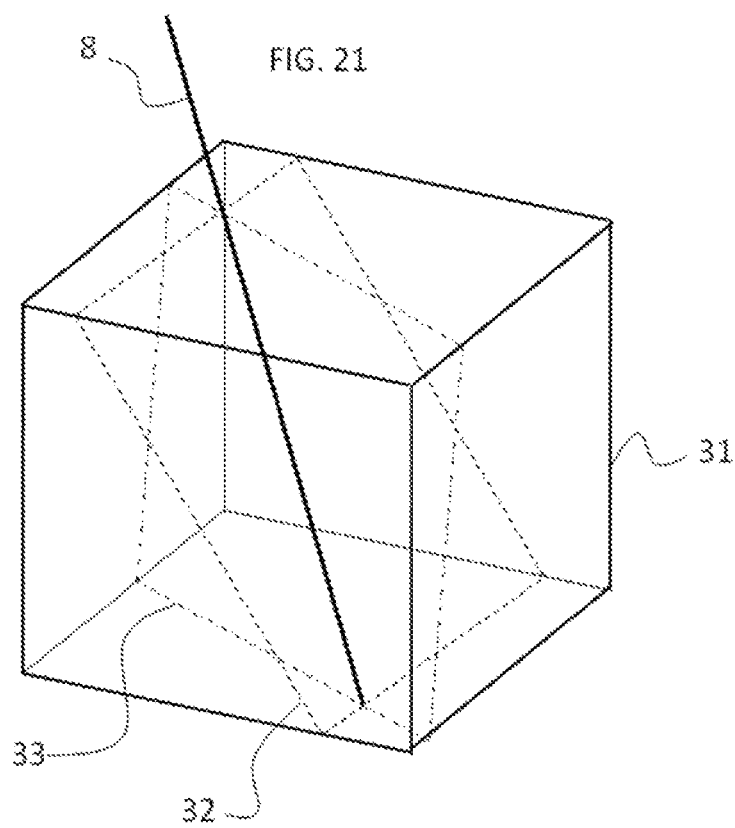
FIG. 21 is a schematic view of the instrument line in the 3D image with two image planes passing through the line

The device of the invention is represented on FIG. 2. It is constructed around a computer 9 that includes all the processing parts of the system. An instrument 8 is placed on the body skin surface 3 before its insertion inside the body. A calibration support 6 is fixed on the skin of the body 3. In a preferred embodiment, the back face of the calibration support 6 comprises adhesive material that is biocompatible and used commonly on medical tapes. In another preferred embodiment represented on FIG. 14, the back face of the calibration device 6 comprises a large suction pad made of silicon with a depression provided by a pump 23 manually activated until there is enough adhesion between the skin and the calibration support, this embodiment having the advantage of avoiding to remove the adhesive tape, which is particularly advantageous if the position of the calibration support needs to be readjusted one or several times. In a preferred embodiment, a semi-rigid element is placed between the calibration support and the lower face, that is adhesive face or a suction system, said semi-rigid element being able to conform to the skin of the body in order to obtain a better adherence. Such semi-rigid element can be for instance a material commonly used for soft cast. In another preferred embodiment, the lower face of the calibration support comprises at least three legs that are in contact with the skin, each leg comprising an adhesive surface or a suction system. Three of said legs are represented in FIG. 7 in a preferred embodiment wherein the calibration support 6 is a ring. The calibration support 6 carries one or several micro-cameras 7 that are rigidly connected. In a preferred embodiment, the calibration support and the cameras are fixed together and cannot be disassembled, which has the advantage of simplicity and minimal size. In another preferred embodiment represented in FIG. 15, the calibration support comprising the fiducial markers is fixed to the skin and the cameras are mounted on an intermediate basis 25 that can be fixed in a reproducible and accurate manner to the calibration support. In a preferred embodiment, the reproducible fixation between the calibration support 6 and the intermediate basis 25 is achieved by permanent magnets included in the calibration support and also constituting specific fiducial markers visible on the 3D image. In another preferred embodiment, the reproducible fixation is achieved by mechanical means, as illustrated on FIG. 14, wherein an elliptical hollow 24 has been performed in the calibration support 6 and wherein a male part perfectly adjustable to such elliptical hollow, and not represented, is fixed to the lower part of the intermediate basis 25, using a clipping mechanism between two plastic components. Many other reproducible fixation mechanisms can be proposed. This preferred embodiment using the intermediate basis has the advantage to offer the possibility to remove the micro-cameras when the body is going to be translated in the imaging device 1; this eliminates artefacts potentially created by the micro-cameras on the medical images, it also protects the cameras from the physical effects induced by the imaging device, such as radiation for CT or magnetic strengths for MR images, and during the 3D image acquisition, it also eliminates the presence of the wires 10 that link the micro-cameras to the computer 9 of the device in a preferred embodiment, as illustrated on FIG. 2. The micro-cameras can be only one or several as it will be further detailed. In a preferred embodiment, a wire 10 is connecting the output of the micro-cameras, which is usually a digital output, to the computer 9 of the device. The wire 10 also brings the necessary power supply to the cameras and their accessories such as miniature light projectors 46, as illustrated in FIG. 16. In another preferred embodiment, the basis of the micro-cameras 7 contains an electronic board that comprises a battery for providing power to the micro-cameras but also a high speed wireless connection and transfer of the video images towards the computer 9, which has the advantage to eliminate all cables. The placement of an instrument 8 into a body 3 is usually performed in sterile conditions. In a preferred embodiment, the micro-cameras 7 are cleaned and sterilized before using conventional means such as ethylene oxyde, or gamma rays, or plasma. In another embodiment, the device comprises a transparent sterile drape, not represented, that covers the micro-cameras totally. The transparent plastic part that comes in front of the optics of the micro-cameras is flat, either by tightening the plastic bag under tension, or by using a blister that can be clipped to the optics. The medical images of the body are produced and stored in the computer 4 of the medical imaging device 1. Those images are transferred to the computer 9 via an Ethernet link using DICOM well established standard protocol. The computer 9 of the device has a video output monitor 12 on which various representations of the instrument and the medical images of the body can be displayed together, just in front of the user, on the side of the body. The body images show structures 13 represented on the display monitor 12, such as organs, bones, vessels, tumors, cysts and any other data and information useful for placing an instrument towards a target and avoiding obstacles and dangerous structures. The real instrument 8 is displayed on the display monitor 12 using various representations 14. In a preferred embodiment, an average axis is computed that approximates the instrument by a line in a best fit method such as least squares. Two 2D images passing through said axis are computed in the volume of the 3D images. This conventional principle of surgical navigation is illustrated in FIG. 21. Two planes 32 and 33 passing through the instrument average axis are computed in the volume of the 3D image 31 and then the two images corresponding to said planes are displayed on a monitor 12 to provide the user with a 3D representation. The user is then able to visualize and predict where the instrument will pass with respect to the anatomical structures 13 if it is inserted in the body with its current position and orientation prior to any incision. The instrument position and orientation is then modified and adjusted accordingly in order to respect the specific objectives and criteria of the user, which is usually to reach a predefined target such as a tumor whilst avoiding perforation of dangerous structures such as lungs for instance. This visualization helps the user targeting structures with ease and rapidity, also avoiding repetitive acquisitions of 3D images which generate extra time and other effects such as radiation.

Figure 22:
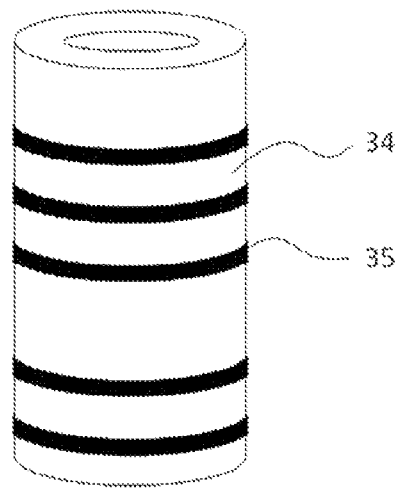
FIG. 22 is a schematic view of a preferred embodiment of the invention wherein a guide comprises specific rings for reliable detection

In a preferred embodiment shown in FIG. 2, two micro-cameras 7 are assembled to constitute a stereoscopic pair. This configuration is light, easy to handle in many locations of a body, and it is easy to manufacture. Having two micro-cameras makes it easy to reconstruct by software included in the computer 9 the 3D shape of the instrument using well known stereoscopy algorithms. In another preferred embodiment, only one of those two micro-cameras shown in FIG. 2 is used to reconstruct the position and orientation of a linear object on which specific features having a known three-dimensional geometry, such as rings 49 shown in FIG. 8 that are provided to reinforce the visibility of the instrument, have been set. This embodiment with one camera represents the most simple and cheap implementation of the invention, but it requires adding features such as rings 49 on the instrument or on the guiding tool, such as the rings 35 shown on the guiding tool 34 in FIG. 22 that reinforce the visibility of the instrument. Indeed, although a linear infinite axis cannot be located with only one camera, the centers of the rings set on the instrument or the guide constitute points in three dimensions with a known geometry that can be reconstructed by standard mono-camera algorithms commonly used in computer vision.

Figure 3:
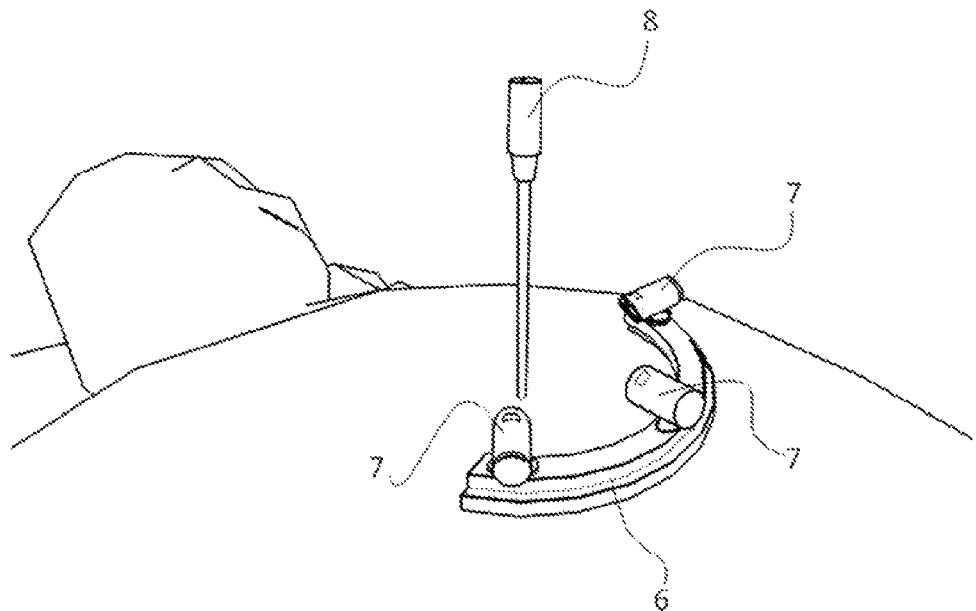
FIG. 3 is a schematic view of a preferred embodiment of the invention with three micro-cameras.

In another preferred embodiment shown in FIG. 3, three micro-cameras 7 are assembled together on an arc of a ring 6 that constitutes the calibration support. This configuration provides redundant information since only two cameras are sufficient in theory. But when the user holds the instrument, fingers and gloves can obstruct the visibility of the cameras in some parts of the video images. Having three cameras reinforce the probability to see enough portions of the instrument 8 on the video images to make possible its detection and determination of its position.

Figure 4:
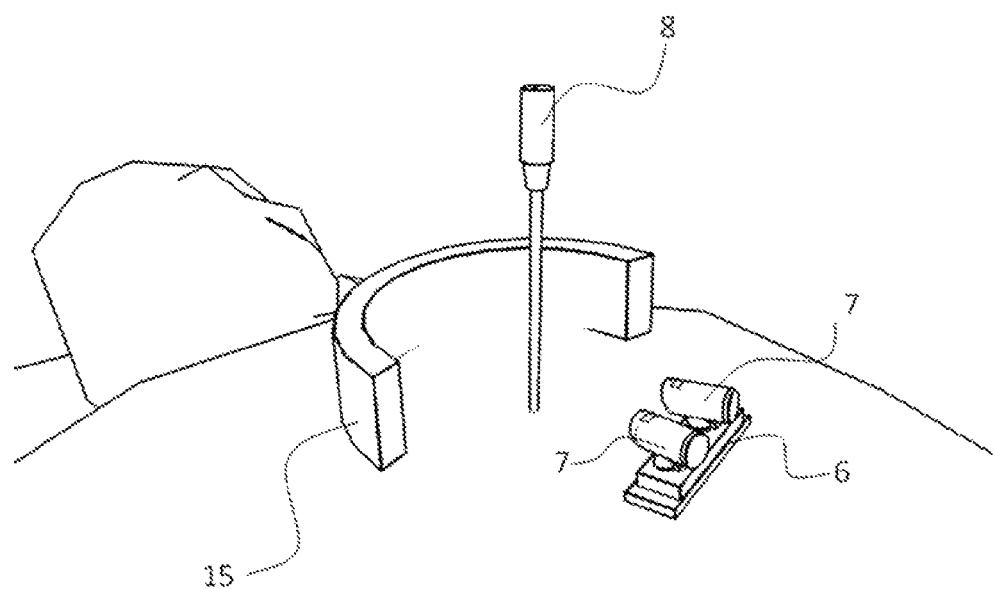
FIG. 4 is a schematic view of another preferred embodiment of the invention with two micro-cameras and a background support.
Figure 5:
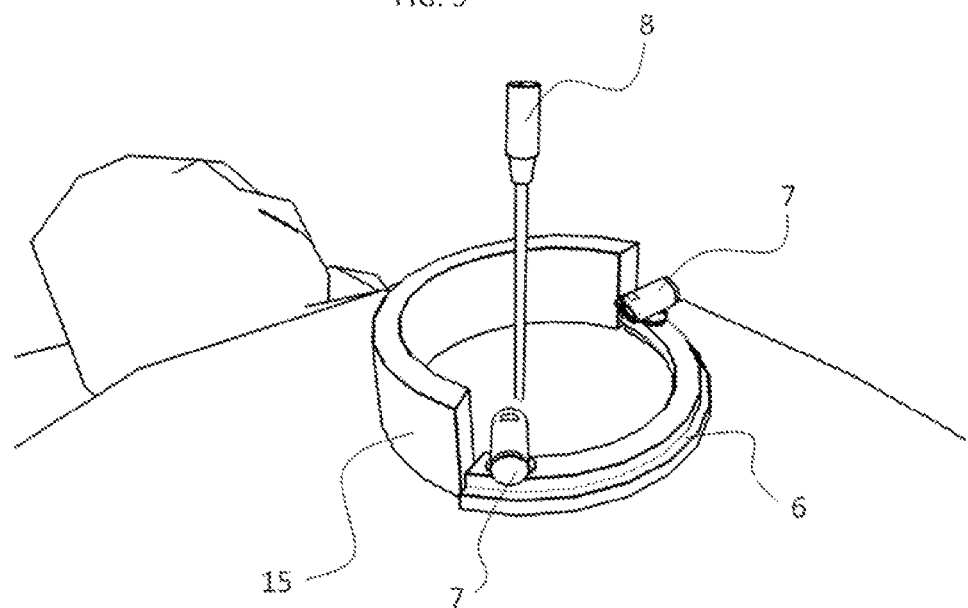
FIG. 5 is a schematic view of another preferred embodiment of the invention with two micro-cameras and a background support attached.

In a preferred embodiment shown on FIG. 4, a background element 15 is placed in front of the cameras, such that the background element is behind the instrument in the field of view of the cameras. The background element has a known color contrasting with the instrument that reinforces the contrast of the instrument on the video images, in order to make the instrument detection more robust and avoid artefacts that could be apparent in the background of the image. As shown in FIG. 5, the background element 15 and the calibration support 6 can be rigidly attached together in order to simplify their relative positioning by the user.

In another preferred embodiment, four micro-cameras 7 are fixed together around a ring that serves as the calibration support of the device. This set up increases the robustness of detection of the instrument and allows for any manipulation and fingers positioning from the user. As shown in FIG. 7, the ring can also comprise a background element 15 all around its surface.

In a preferred embodiment as shown in FIG. 7, the background element 15 comprises video calibration markers 47, which constitute elements of a calibration grid, not to be confounded with the fiducial markers comprised in the calibration support. Those video calibration markers have a known spatial arrangement and geometry in three dimensions such that they can be used to calibrate the micro-cameras automatically and at any time, using conventional video cameras calibration methods cited in the Background section. The video calibration markers must have specific shapes and contrast, such as cross-hairs, but also simple black and white squares on a chessboard, patterns with lines and bands, circles, or dots. The calibration support and the calibration grid of the video cameras are rigidly connected and constitute only one reference system. All micro-cameras are calibrated in this coordinate system associated with the calibration support. This can advantageously compensate from any deviation of the micro-cameras optical or electronic parameters and also from any motion of the cameras relative to each other if the structure of the ring has some small flexibility which can induce rotations of the optical axis of the cameras that introduce substantial errors in the 3D reconstruction processing. Having the video calibration markers 47 included in the background support 15 can be used in any of the configurations presented in this description, with one, two, three, four or more micro-cameras, in any set up.

Figure 23:
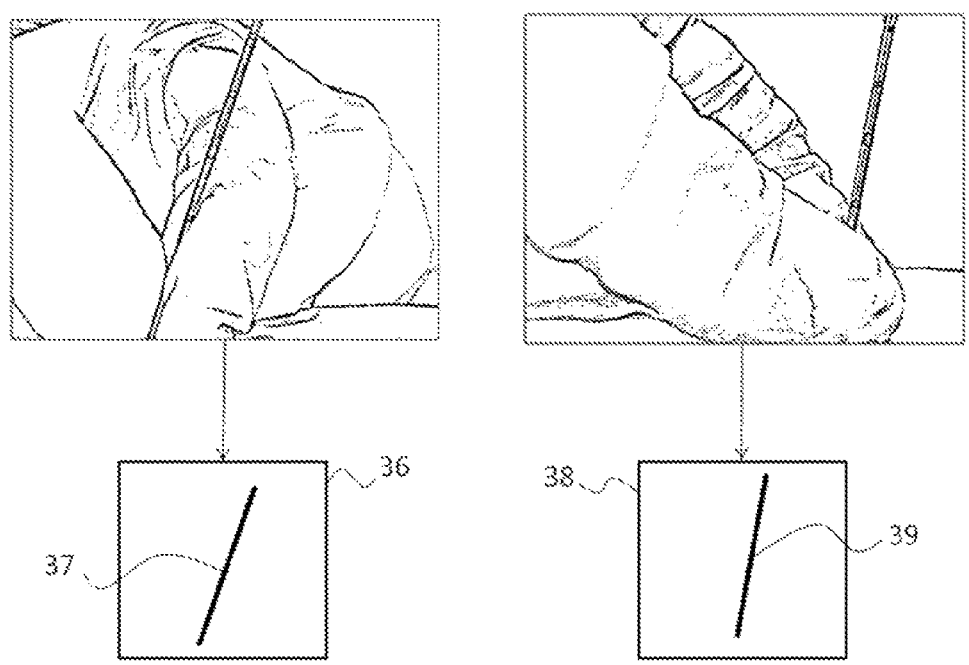
FIG. 23 is a schematic view of the video images that are acquired and processed to detect the instrument line

In a preferred embodiment, the instrument 8 is a conventional needle or trocar that is linear and can be slightly bended. On each image of the micro-cameras, the conventional computer vision algorithms cited in the Background section are used to detect the instrument axis and to reconstruct the 3D line corresponding to the center of the instrument in the reference system of the calibration support, itself being registered with the reference system of the 3D image using conventional registration techniques based on the fiducial markers comprised in the calibration support. The detection of the instrument on the images is performed automatically with an algorithm which is permanently processing the images of the video-cameras and searching for linear thin objects on each image. As shown in FIG. 23 in the instance of two micro-cameras, the best fit line corresponding to the instrument axis is detected on the images 36 and 38 of each micro-camera, providing two line segments 37 and 39 that are used to build the 3D line of the instrument axis in the calibration support coordinate system. If more than two micro-cameras are used, each image provides 2D information with one or more line segments that are back-projected in the 3D coordinate system of the calibration support in order to reconstruct a 3D line that has projections that approximate the detected line segments in a least squares approximation. This consists in finding the 3D line that has projection segments Si on the 2D images for i=1 . . . N where N is the number of micro-cameras such that the sum of squares of distances between the detected segments and the projection segments Si is minimal, with an elimination of outliers by removing distances that exceed a given threshold in order to remove false detection of segments. This is only one example of a possible algorithm and many more refinements and variations can be added and substituted.

Figure 17:
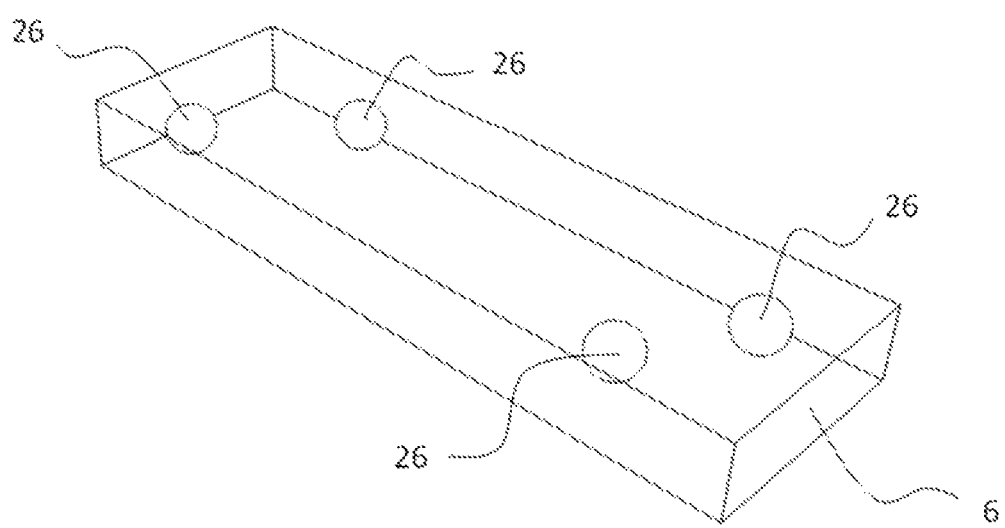
FIG. 17 is a schematic view of a preferred embodiment of the calibration support with fiducial markers made of balls.

In a preferred embodiment, as shown in FIG. 17, the fiducial markers of the calibration support 6 are at least three spherical balls 26 spatially arranged in a known position that can be recognized in a unique manner. The balls 26 are detected automatically or interactively on the 3D image using conventional processing for sphere detection. Pair-points matching techniques are used to compute the transform between the coordinate system of the 3D image and the coordinate system of the calibration support in which the three balls have known coordinates by design and manufacturing. More than three balls 26 are used to augment accuracy and robustness of the method using least squares fitting methods, typically four, five, six or ten. The registration methods and algorithms that are used for our processing are known in the Background technology, for instance using one of the numerous methods cited in the review "J B A Mainz and M Viergever, *A survey of medical image registration, Medical Image Analysis* (1998), vol 2, n 1, pp 1-36."

Figure 18:
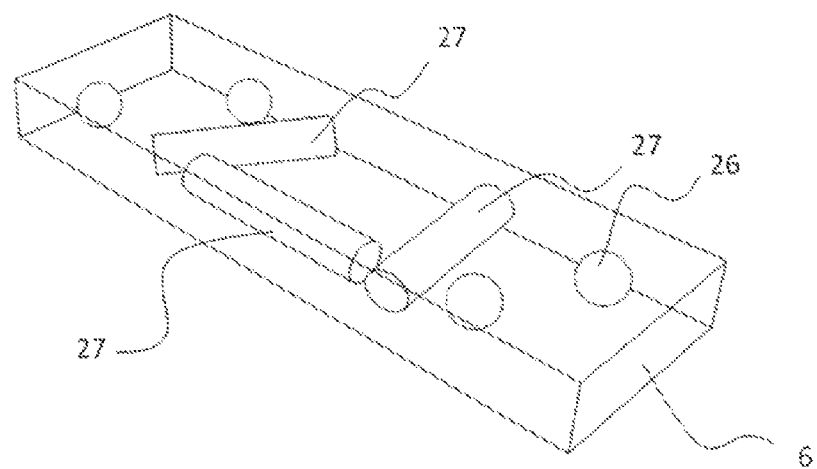
FIG. 18 is a schematic view of a preferred embodiment of the calibration support with fiducial markers made of balls and cylindrical elements

In another preferred embodiment, as shown in FIG. 18, the fiducial markers of the calibration support are at least two non-parallel cylindrical tubes 27 spatially arranged in a known position that can be recognized in a unique manner. The tubes can be made of aluminum or of hollow portions of plain plastic parts, for CT images, or filled with high contrast medium such as gadolinium, for MR images. After detecting the centers of the tubes on the 3D images, a line-to-line matching algorithm is used to obtain the transform between the 3D image coordinate system and the calibration support coordinate system. In another preferred embodiment, also shown in FIG. 18, the fiducial markers are a combination of cylindrical tubes 27, cylindrical discs and spherical balls 26 arranged in a known position that can be recognized in a unique manner.

In a preferred embodiment already mentioned above, the instrument 8 is a conventional needle with no particular features. However, in order to improve the robustness of the detection algorithm of the instrument on each image, which means reducing false detection due to parasite lines or thin objects like wires on the images, and improving the detection rate of the presence of the instrument instead of declaring a false absence, it is advantageous to add a reinforced visibility element on the instrument.

Figure 8:
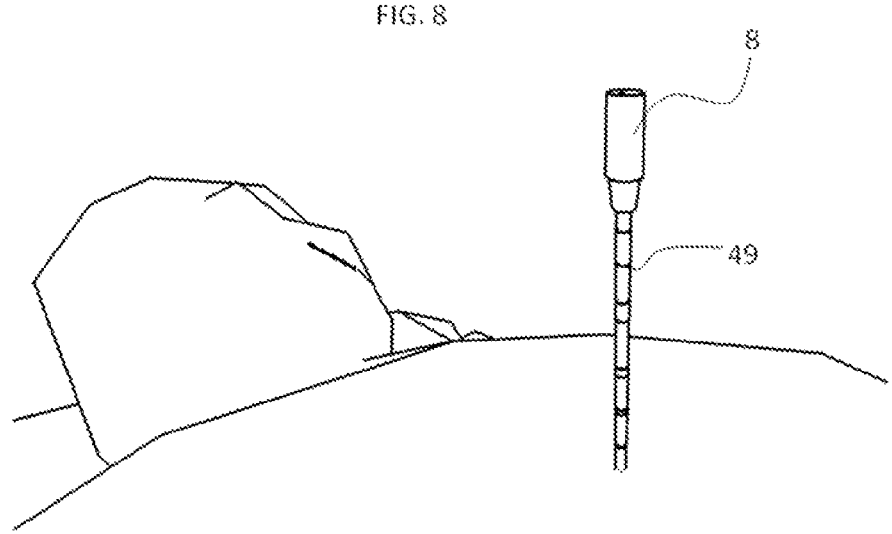
FIG. 8 is a schematic view that represents an instrument with engraved landmarks.

In a preferred embodiment, as shown in FIG. 8, the instrument 8 comprises reinforced visibility elements 49, e.g. in the shape of annular rings, directly engraved on the instrument external surface. That embodiment also corresponds to the situation where a conventional needle has specific marks engraved on its axis in order to provide information about depth penetration. The positions of the specific marks along the needle axis are simply recorded in the memory of the computer for that particular instrument. One possible method to enter those data is simply to present the instrument in front of the micro-cameras at the beginning of the intervention with particular care to avoid occlusion by the fingers and other objects, and then the video images are processed to extract the position of the landmarks and rings on the instrument surface. If the tip is also visible during this calibration step, the position of the landmarks is determined with respect to the tip so that information about the tip position will be also displayed on the 3D image once the landmarks have been identified during the instrument insertion.

Figure 9:
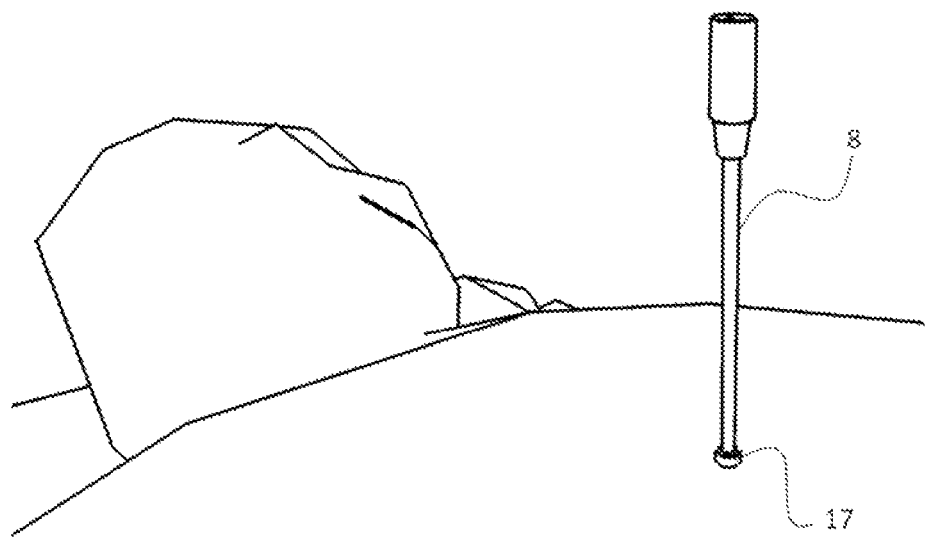
FIG. 9 is a schematic view of a preferred embodiment of the invention wherein a ring is used to facilitate the detection of the instrument.

In another preferred embodiment, as shown in FIG. 9, the reinforced visibility element is a reinforced visibility ring 17 distinct from the instrument having a donut shape and wherein the instrument 8 has a linear part passing through the hole of the reinforced visibility ring. The reinforced visibility ring 17 is for instance a ring having a specific color like bright green or bright yellow that is easy to detect on the color video images of the micro-cameras. The algorithm then searches for a linear and thin object that passes through the center of the green or yellow ring on each image which reduces significantly the probability to detect a false object having a linear shape such as a thin wire, the edge of an object, or a shadow. Once the instrument is detected at the level of the ring on one or several video images, the instrument is tracked on the image as a thin and linear object that can be slightly bended continuously from the starting point. If a finger or other object interrupts the tracking of the instrument from its basis, the algorithm searches for segments in the prolongation of the previously found segment. The ring 17 can be fixed to the skin by adhesive back face once the entry point has been determined, or it can simply slide around the instrument axis with enough play to let the instrument slide with no friction or with moderate friction. If there is friction, the ring will be stopped by the skin surface during the instrument insertion so that it does not create any risk.

Figure 10:
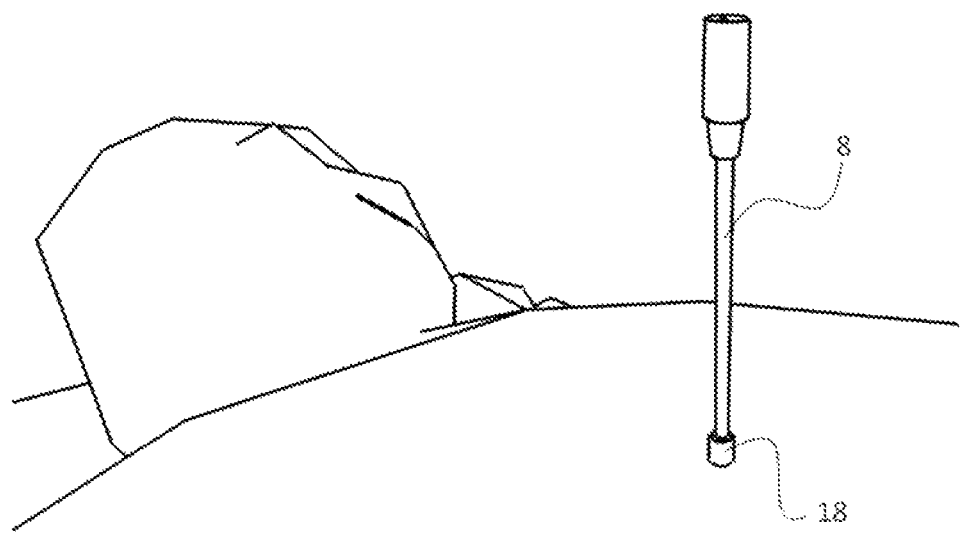
FIG. 10 is a schematic view of another preferred embodiment of the invention wherein a cylindrical guide is used to facilitate the detection of the instrument.
Figure 12:
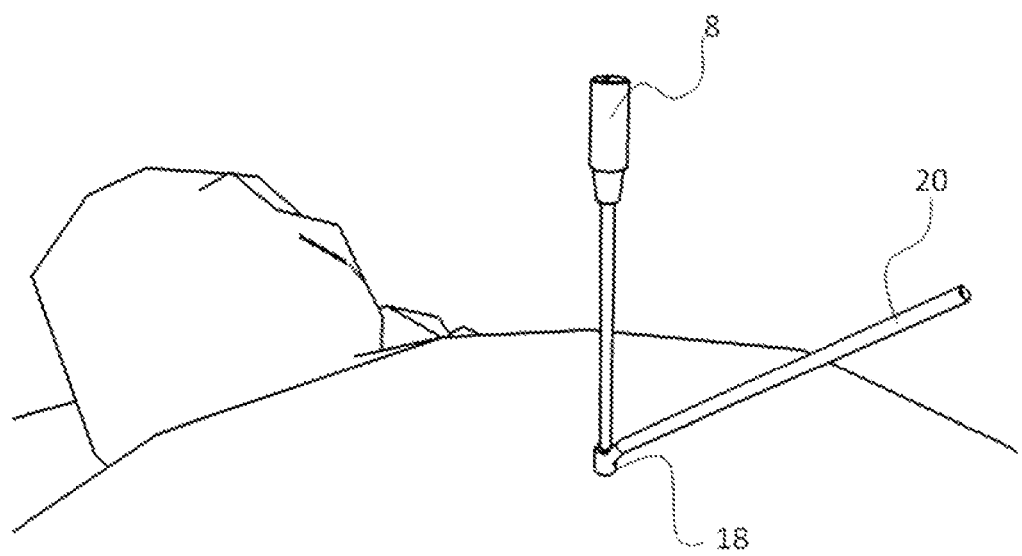
FIG. 12 is a schematic view that represents another embodiment of a cylindrical guide with a handle

In another preferred embodiment, as shown in FIG. 10, the reinforced visibility element comprises a reinforced visibility cylindrical guide 18 wherein the instrument 8 has a linear part passing through the reinforced visibility cylindrical guide 18. This is a similar concept to the previous one and all details mentioned for the ring apply to the cylindrical guide. But the advantage of that embodiment is that the detection of a known cylinder on the video images provides a point and a direction in which the instrument has to be searched, which reduces even more the probability to obtain a false detection of the instrument. A short cylinder provides a cone of possibilities in which the instrument axis has to be searched. For ease of manipulation, as shown in FIG. 12, the cylinder 18 can be equipped with a handle 20.

Figure 11:
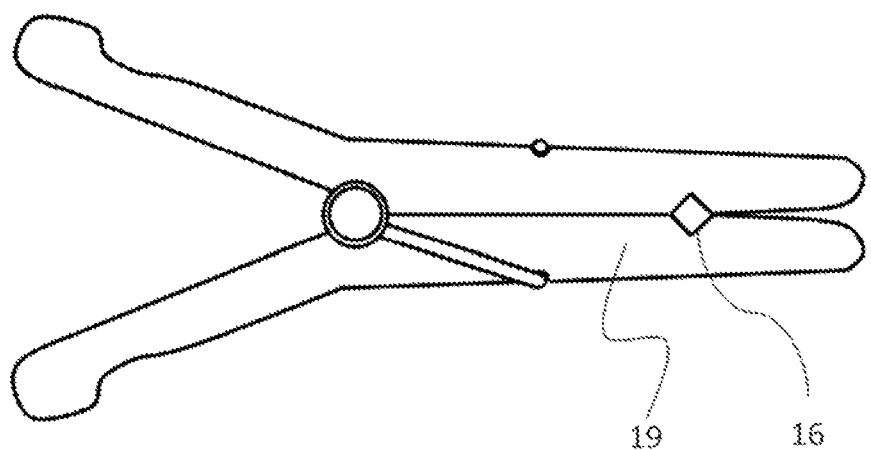
FIG. 11 is a schematic view that represents a peg for guiding the instrument.

In another embodiment, as shown in FIG. 11, the instrument is guided by a guiding device having a clothes peg shape 19 wherein the articulated branches of the peg comprise a V-shaped groove 16 for guiding the linear part of the instrument. The peg applies a constant pressure on the groove 16 that guides the instrument. It has a known 3D solid geometry from design and manufacturing, and a specific color like bright green or pink. The unique geometry of the peg makes it impossible to confound with another object on the video images. Its detection benefits from computer vision algorithms cited in the Background section and intended to detect and localize a complex rigid object made of multiples planar surfaces and edges. The opening of the peg necessitates detecting and localizing the two branches of the peg independently under the constraint that they have a common axis. Once the peg has been identified and detected, the algorithm searches for an instrument in the region of the groove 16 of the peg.

Figure 13:
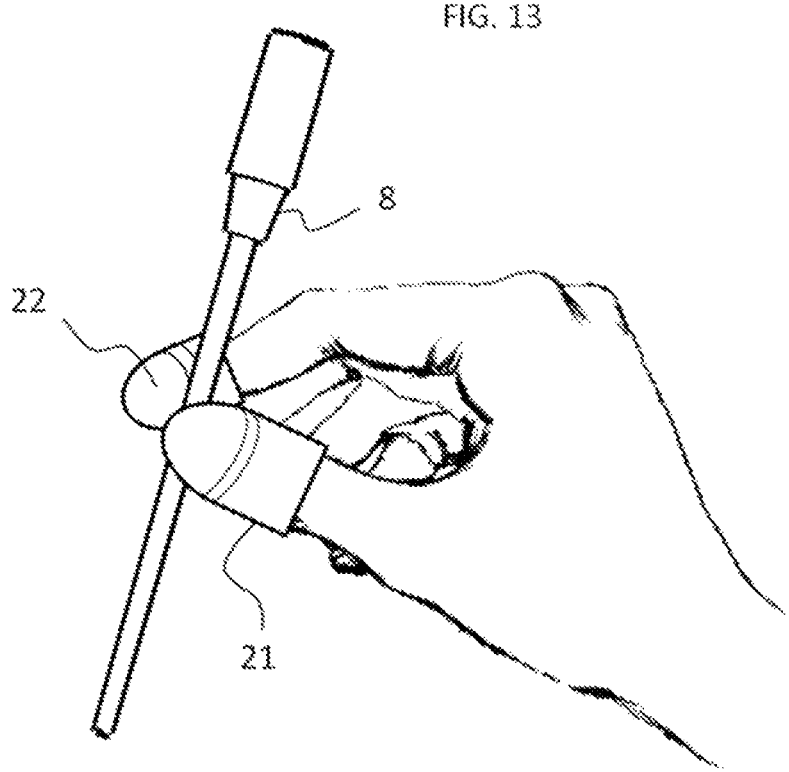
FIG. 13 is a schematic view that represents another embodiment of the invention with specific elements on finger tips.

In another embodiment, as shown in FIG. 13, the reinforced visibility elements are made of at least one reinforced visibility glove finger extremity. An element like a thimble 21 or 22 is fixed to one or two fingers on top of sterile gloves, it has a known color, pattern and shape which make it easy to identify on the video images. The linear instrument is then searched in the vicinity of those detected shapes. If the thimble-like element has been set to two fingers that carry the instrument, the instrument is searched between the two elements. The thimble-like element is rigid or semi-rigid.

In another embodiment, as shown in FIG. 16, the micro-cameras are equipped with a lighting system 46 that reinforces the visibility of the instrument on the video images by lighting the instrument. In general, the instrument is a metallic cylindrical object that offers specular reflection and therefore the incident light coming from a source fixed above or near the camera optical center will produce a bright line shining on the instrument axis, which is easy to detect on the video images by algorithms of detection of edges using a Canny-Deriche filter for example.

In another preferred embodiment, the lighting system 46 is emitting light in a non visible infra-red spectrum which offers the advantage to avoid perturbing the eye of the user and still reinforcing the contrast on the video images since most video cameras are sensitive to infra-red light, provided however, that any filter in that spectrum has been removed from the camera optics.

Figure 6:
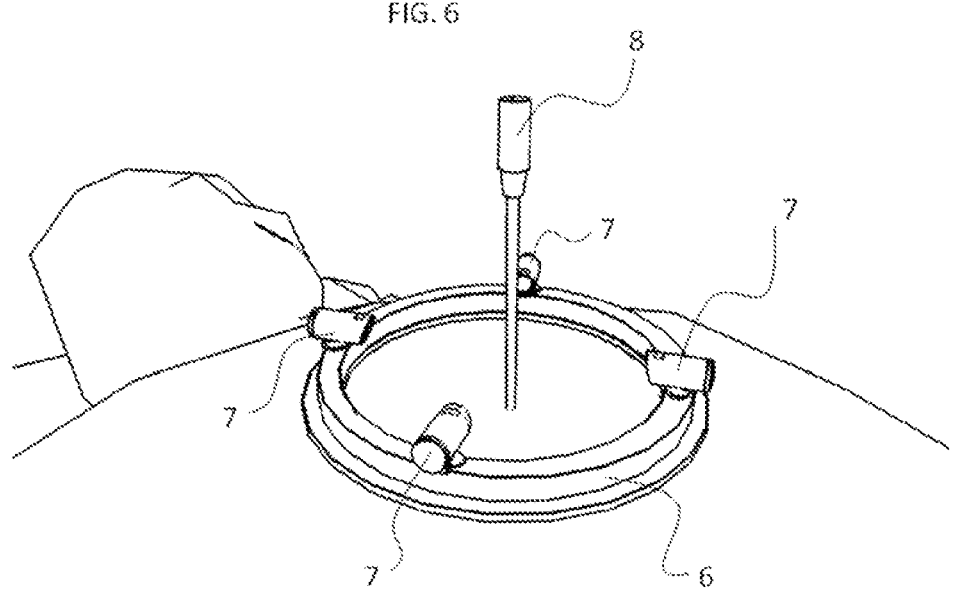
FIG. 6 is a schematic view of another preferred embodiment of the invention with four micro-cameras.
Figure 19:
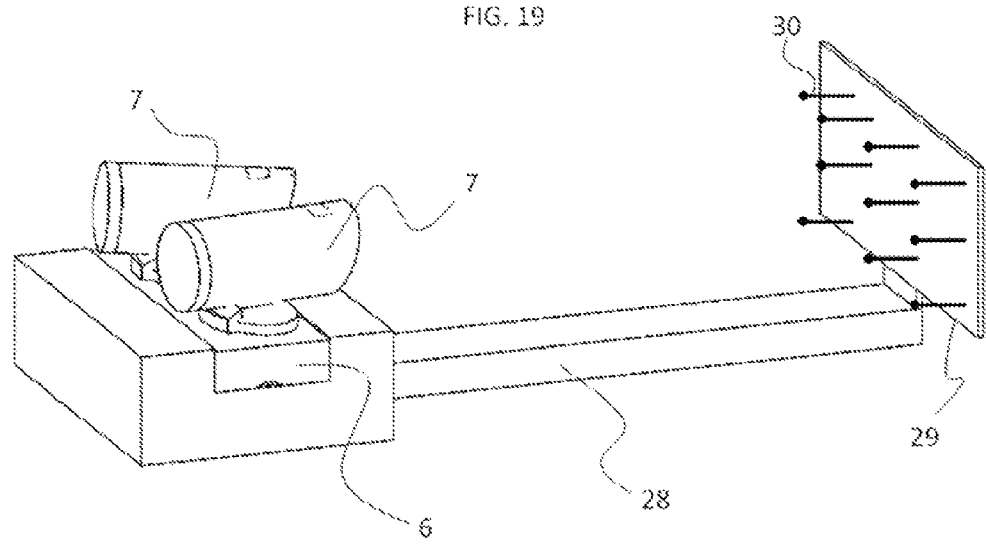
FIG. 19 is a schematic view of a calibration phantom mechanically connected to micro-cameras

For calibrating the video cameras, which means obtaining their spatial extrinsic geometry in the coordinate system of calibration support, a method has been described above by using video calibration markers 47 directly included in the background support 15. It is assumed that the intrinsic calibration model of the micro-cameras that comprises the value of the focal lens and the lens distortion parameters is stable and known by manufacturing and factory calibration of each individual camera. In another preferred embodiment, a specific calibration phantom is used to perform the complete camera calibration for intrinsic and extrinsic parameters using one of the conventional algorithms and methods cited in the Background section for automatic calibration of cameras. As shown in FIG. 19 for an embodiment with two micro-cameras, the calibration phantom 29 which is used to determine the geometric relationship between a calibration support 6 and micro-cameras 7 comprises an extension bar 28 connected in a reproducible and known manner to the calibration support, a plurality of video calibration markers 30 rigidly connected to the extension bar 28 and visible on the video images obtained from the micro-cameras and spatially arranged in a known position that can be recognized in a unique manner. The video calibration markers 30 are typically cross hairs or balls or corners of black and white squares of a chessboard. They are arranged at known precise spatial positions on a planar grid that is easy to manufacture, although non planar arrangements are also possible. By design and manufacturing, the coordinates of the video calibration markers 30 are known in the coordinate system of the calibration support 6 which is rigidly connected to the calibration phantom 29. The calibration process of the cameras is applied to provide a transform between the pixel of each video image and a corresponding back projection 3D line in the coordinate system of the calibration support. This embodiment of calibration device and method can be applied to any configuration using one, two, three, four or more cameras. For four cameras located on a ring as shown in FIG. 6 or FIG. 7, the calibration phantom 29 has a cylindrical shape and is located in the middle of the ring, with a rigid bar connecting the calibration phantom to the ring, and a plurality of video calibration markers mounted all around the cylindrical shape.

Figure 20:
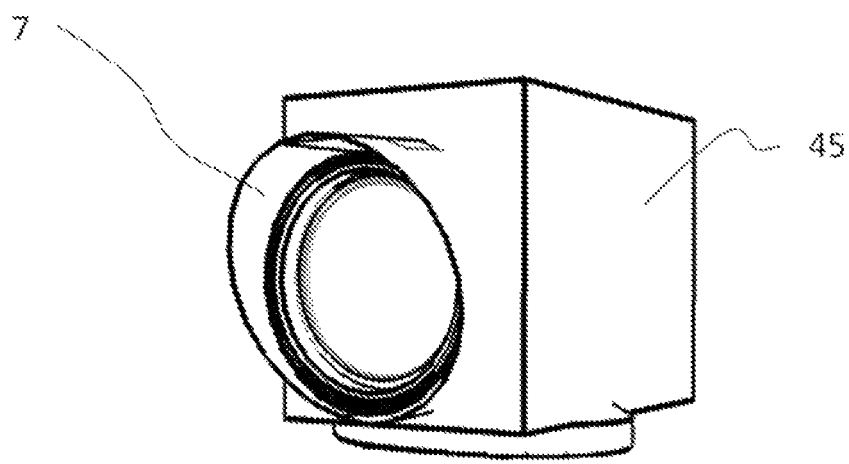
FIG. 20 is a schematic view of a micro-camera with reinforced shielding

In a preferred embodiment, the 3D image is a MR image obtained with a tunnel or open magnetic imaging device. The detachable embodiment shown in FIG. 15 makes it possible to avoid passing the micro-cameras inside the imaging device. However, if a compact solution is preferred, with micro-cameras permanently attached to the calibration support, the micro-cameras need to have a specific protection against radiofrequency and magnetic energy produced by the MR device. As shown in FIG. 20, each micro-camera 7 is protected by a dedicated shielding 45.

Figure 24:
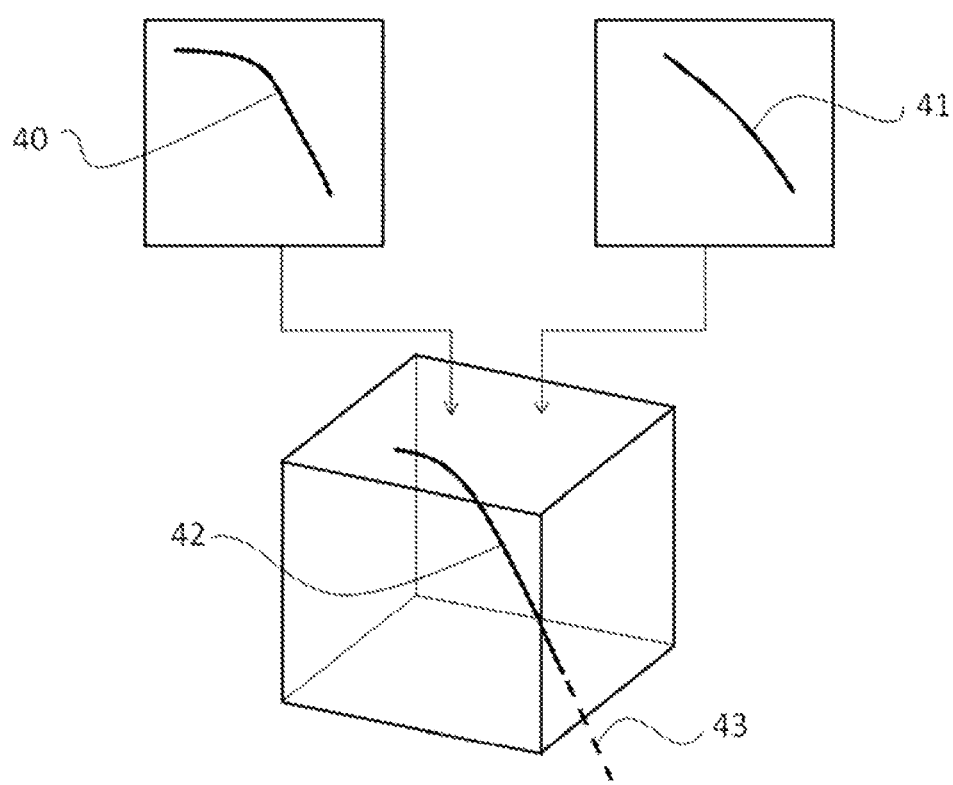
FIG. 24 is a schematic view of the reconstruction of a curved instrument in the 3D image from two video images

In all embodiments described above, the instrument can be slightly flexible. As shown in FIG. 24 for an embodiment with two micro-cameras, the curved segments 40 and 41 corresponding to the curved instrument are detected on both video images. For stereoscopic arrangements with two cameras, each point on a curved line segment is paired with another point of the other curved line segment and provides a 3D point in the calibration support coordinate system. By combining all points reconstructed by this mechanism together, a 3D curve 42 is reconstructed in the coordinate system of the calibration support. Said 3D curve can be also extended with a dashed line 43 to predict its potential direction in the 3D image. The portion of the 3D curved line which is the closest from the patient skin is used to compute the straight line that approximates the best the curved line in order to offer a conventional display with two images as represented in FIG. 21.

In another embodiment, the insertion of the instrument can be performed in a room separated from the room where the 3D image is acquired. It is then necessary that the basis of the calibration support stays in a fixed position relative to the body. More precisely it means that the motions of the basis of the calibration support with respect to the target must be negligible with respect to the accuracy required by the user and corresponding to the intended use. All the other steps and devices then remain the same as described above.

All the embodiments presented above are intended to reinforce the precision and robustness of the detection and reconstruction of the instrument. They all offer specific advantages for the user in terms of ergonomics, but also for the manufacturer in terms of cost, such that several of those embodiments can be offered for sale with different pricing and options in order to accommodate for the individual user preferences and trade-off.

The invention claimed is:

1. A method for per-operatively determining the position of a linear instrument with respect to medical images of a body, the method comprising the steps of :
   a. placing a calibration support comprising fiducial markers on the skin of the body in the intended region of interest;
   b. acquiring the medical images of the body with calibration support in place;
   c. detecting the fiducial markers on the medical images to determine the geometric relationship between a coordinate system attached to the medical images and a coordinate system attached to the calibration support;
   d. connecting rigidly at least one micro-camera to the calibration support at a known position;
   e. placing a linear instrument in the field of view of the at least one micro-camera;

f. detecting in real time the linear instrument in the video images of the at least one micro-camera by searching linear or curvilinear segments in the video images and by constructing a 3D line or curve corresponding to the axis of the linear instrument based on said linear or curvilinear segments;

g. calculating in real time the position of the linear instrument in a coordinate system attached to the at least one micro-camera using the calibration of each micro-camera in the coordinate system of the calibration support; and h. transferring the position of the linear instrument in the coordinate system attached to the medical images using the result of step (c).

2. The method of claim 1 further comprising the step of displaying the position of the linear instrument on medical images.

3. The method of claim 2 wherein two reformatted images passing through the linear instrument axis are computed in the volume of medical images and displayed.

4. The method of claim 1 wherein the calibration of the at least one micro-camera is determined by a method that comprises the steps of:

a. connecting to the calibration support a calibration phantom that comprises an extension bar and a plurality of markers rigidly connected to the extension bar and visible on the video images obtained from the at least one micro-camera and spatially arranged in a known position that can be recognized in a unique manner in a phantom coordinate system;

b. acquiring video images of the markers of the calibration phantom;

c. determining the projection matrix for each micro-camera using the known coordinates of the markers in the phantom coordinate system;

d. transferring the projection matrix of each micro-camera in the calibration support coordinate system by using the geometric matrix between the calibration support coordinate system and the phantom coordinate system determined by metrological measurements performed when the calibration support and the calibration phantom are connected together.

5. The method of claim 1 further comprising the step of reinforcing the visibility of the linear instrument for its detection using one or several of the following means:

a. adding an infrared light system to the at least one micro-camera that lights the linear instrument;

b. adding a background element with a known color contrasting with the instrument behind the linear instrument.

6. The method of claim 1 further comprising a step of reinforcing the visibility of the instrument for its detection using a reinforced visibility element in relation to the linear instrument, said reinforced visibility element having one or several of the following features:

a. a specific and known color
b. a specific and known shape
c. a specific and known pattern
d. a specific and known dimension.

7. The method of claim 1 wherein the linear instrument has a known internal axis that guides a needle and an external reinforced visibility element made of an external shape that is colored, complex, and specific.

8. The method of claim 1 wherein the linear instrument is a conventional needle and the needle axis is detected on the video images by searching for long and thin objects in the video images.

9. The method of claim 1 wherein the deformation of the linear instrument axis is determined and reconstructed in three dimensions for use in either one or several of the following modes:

a. inform the user about excessive instrument deformation
b. extend instrument deformation measured externally inside the body to predict and display the trajectory of the linear instrument on medical images.

10. The method of claim 1, wherein step (a) consists in attaching the calibration support to the skin of the body.

11. The method of claim 1, wherein step (d) comprises attaching at least two micro-cameras to the calibration support.

* * * * *